United States Patent [19]

Fuchs et al.

[11] Patent Number: 5,360,905
[45] Date of Patent: Nov. 1, 1994

[54] RECOVERY OF CAPROLACTAM FROM OLIGOMERS AND/OR POLYMERS OF CAPROLACTAM

[75] Inventors: Hugo Fuchs; Claus-Ulrich Priester, both of Ludwigshafen; Gerald Neubauer; Erwin Brunner, both of Weinheim; Josef Ritz, Ludwigshafen; Michael Kopietz, Gruenstadt, all of Germany

[73] Assignee: BASF Aktiengesellschaft, Ludwigshafen, Germany

[21] Appl. No.: 60,972

[22] Filed: May 14, 1993

[30] Foreign Application Priority Data

May 21, 1992 [DE] Germany ............... 4216848

[51] Int. Cl.$^5$ .................................. C07D 201/12
[52] U.S. Cl. .................................................. 540/540
[58] Field of Search ...................................... 540/540

[56] References Cited

U.S. PATENT DOCUMENTS

| | | | |
|---|---|---|---|
| 4,360,461 | 11/1982 | Fuchs et al. | 540/540 |
| 4,605,762 | 8/1986 | Mandoki | 540/540 |
| 4,683,305 | 7/1987 | Fuchs et al. | 540/533 |

FOREIGN PATENT DOCUMENTS

| | | |
|---|---|---|
| 048340 | 3/1982 | European Pat. Off. |
| 819683 | 9/1959 | United Kingdom |

OTHER PUBLICATIONS

Chem. Abst. vol. 88, No. 24, Jun. 12, 1978, Abstract No. 170756k, Dmetrieva L. A. et al., "Caprolactam from Capron Fiber Production", p. 18.

*Primary Examiner*—Robert T. Bond
*Attorney, Agent, or Firm*—Keil & Weinkauf

[57] ABSTRACT

A process for recovering caprolactam from oligomers and/or polymers of caprolactam comprises the following steps:

a) treating oligomers and/or polymers of caprolactam with from 1 to 20 parts by weight of water per part by weight of oligomer or polymer at from 200° to 350° C. under superatmospheric pressure with a residence time of from 0.5 to 10 hours to form an aqueous reaction mixture comprising polycaprolactam, monomeric caprolactam and oligomers thereof, and b) passing the aqueous reaction mixture obtained in a) into a fluidized bed of alumina at from 250° to 400° C. to obtain a mixture of steam and caprolactam.

9 Claims, No Drawings

RECOVERY OF CAPROLACTAM FROM OLIGOMERS AND/OR POLYMERS OF CAPROLACTAM

The present invention relates to a process for recovering caprolactam from oligomers and/or polymers of caprolactam by hydrolyric cracking of oligomers and/or polymers of caprolactam with water.

The production of polycaprolactam and its processing from the melt, for example into filaments by spinning, into film by extrusion or into three-dimensional articles by injection molding, does of course give rise to waste polycaprolactam which needs to be disposed of. Ultimately, furthermore, the articles produced from polycaprolactam with or without further processing, i.e. injection and extrusion moldings, films, packaging and fabrics, need to be disposed of as well after use. It would make sense to find a way of disposing of polycaprolactam and at the same time obtain caprolactam.

U.S. Pat. No. 4,605,762 discloses a process for the hydrolyric cracking of polycondensates wherein polycondensates such as polyesters, nylon-6,6 or polycaprolactam are cracked at from 200° to 300° C. under superatmospheric pressure using from 2 to 20 times the amount of water. Since complete cracking is not achieved, there always remains an appreciable residue comprising oligomers and uncracked polycaprolactam. In addition, there is no disclosure in said U.S. patent as to how the quality of the monomeric caprolactam obtained can be improved so that it can be fed without disadvantage into the purification stage of the caprolactam production process.

EP-A-46 183 discloses cracking caprolactam oligomers, obtained in the extraction of polycaprolactam, at elevated temperatures in a fluidized bed of alumina in the presence of water to form caprolactam monomer. However, there is no disclosure as to how to proceed when not only caprolactam oligomer but caprolactam polymer is present in the aqueous suspension, in particular since the introduction of polymer into a fluidized bed can lead to clumping of the fluidized particles.

It is an object of the present invention to make available a process for recovering caprolactam from oligomers and/or polymers of caprolactam that results in high yields, leaves virtually no residues and, what is more, produces a caprolactam of improved quality that can be introduced without disadvantage into the purification stage of the caprolactam production process.

We have found that this object is achieved by a process for recovering caprolactam from oligomers and/or polymers of caprolactam, comprising the following steps:

a) treating oligomers and/or polymers of caprolactam with from 1 to 20 parts by weight of water per part by weight of oligomer or polymer at from 200° to 350° C. under superatmospheric pressure with a residence time of from 0.5 to 10 hours to form an aqueous reaction mixture comprising polycaprolactam, monomeric caprolactam and oligomers thereof, and then b) passing the aqueous reaction mixture obtained in a) into a fluidized bed of alumina at from 250° to 400° C., preferably from 270° to 400° C., to obtain a mixture of steam and monomeric caprolactam.

The novel process has the advantage that it results in high caprolactam yields and does not in fact leave any residue requiring disposal. Another advantage is that it is not difficult to carry out continuously on an industrial scale. Yet a further advantage is that the quality of the product caprolactam makes it possible to introduce it into the purification step of the caprolactam production process.

According to the invention, the starting material is polycaprolactam which is to be disposed of, for example waste from the production of polycaprolactam or its processing from the melt, for example in the manufacture of yarns or the production of extrudates or injection moldings, or from the production of film and sheet. It is also possible to start from used polycaprolactam articles, such as extrudates, injection moldings or fabrics. Advantageously, the polycaprolactam to be cracked has a particle size of from 1 to 100 mm. This is obtained for example by grinding molded articles which may have been precompacted by heat and pressure.

In the recovery of caprolactam from oligomers or from oligomers and polymers of caprolactam, it is basically possible to use any kind of caprolactam oligomer. It is customary to use oligomers which are formed in the polycondensation of caprolactam, since this reaction generally involves an equilibrium between customarily about 90% by weight of poisoners and about 10% by weight of caprolactam and oligomers. The oligomers, which in general comprise about 50% by weight of dimers and trimers and about 50% by weight of tetramers and higher oligomers, are in general recovered from the aforementioned reaction mixture together with caprolactam by extraction with water.

In stage a) the oligomers and/or poisoners of caprolactam are hydrolyrically cracked with from 1 to 20 parts by weight of water, in particular from 2 to 10 parts by weight of water, per part by weight of oligomer or polymer. Stage a) is carried out at from 200 to 350° C., in particular at from 250° to 300° C. The treatment is effected under superatmospheric pressure, advantageously at from 15 to 200 bar, the superatmospheric pressure being additionally created by forcing in an inert gas, such as nitrogen. It will be readily understood that a liquid aqueous phase is maintained. The treatment is carried out with a residence time of from 0.5 to 10 hours, in particular of from 1 to 5 hours. Furthermore, it is advantageous to use in addition phosphoric acid or an alkali metal hydroxide, in particular sodium hydroxide, in an amount of from 0.001 to 0.1 part by weight per part by weight of oligomer or polymer of caprolactam.

The product obtained in stage a) is an aqueous reaction mixture comprising caprolactam polymer, caprolactam monomer and caprolactam oligomer, The typical composition is for example from 1 to 70% by weight of caprolactam monomer, from 0.1 to 10% by weight of caprolactam oligomer and from 1 to 99% by weight of suspended caprolactam polymer, based on starting oligomer and/or polymer of caprolactam.

The reaction mixture thus obtained in stage a) is passed in stage b) into a fluidized bed of alumina at from 250° to 400° C., preferably from 270° to 400° C., to obtain a mixture of steam and caprolactam.

The reaction mixture of stage a) can be depressurized before being introduced into the fluidized bed, but advantageously the reaction mixture is depressurized directly into the fluidized bed of stage b) via a nozzle opening. The introduction into the fluidized bed can also be effected by injection by means of a nozzle driven by an inert gas.

As alumina it is possible to use the various forms such as argillaceous earth or $\alpha$- or $\gamma$-alumina. $\gamma$-Alumina has proved to make a particularly useful catalyst. The fluidizing gas used is an inert gas such as carbon dioxide, argon or nitrogen, preferably nitrogen. The alumina used advantageously has a particle size of from 0.05 to 1.5 mm, in particular of from 0.1 to 1.4 mm. The fluidized bed height is advantageously chosen in such a way that the residence time of the oligomeric and polymeric caprolactam in the catalyst bed is from 0.1 to 30, in particular from 0.5 to 10, seconds. It is advantageous to carry out the treatment in the fluidized bed at atmospheric pressure. However, it is also possible to employ slightly reduced or slightly superatmospheric pressure, for example from 0.5 up to 2 bar.

The fluidized bed is advantageously maintained at from 290° to 360° C. For this reason it is also advantageous to introduce the inert gas into the fluidized bed at from 290° to 400° C.

The condensables entrained in the gas mixture leaving the fluidized bed are separated off by condensation and then worked up, for example by distillation. It is also possible to pass the aqueous solution obtained directly into the purification stage of the caprolactam production process.

Embodiments of the process of the invention will now be more particularly described by way of example.

EXAMPLE 1

An autoclave was charged with 300 g of nylon-6 and 1,000 ml of water, purged with nitrogen, injected with nitrogen to 5 bar, and heated to 250° C. The total pressure was about 60 bar.

After 5 hours the autoclave contents were cooled down.

The entire contents were then gradually metered into a fluidized-bed oven packed with 600 g of Puralox alumna (Puralox NX a-150, Condea Chemie, bulk density 700–900 g/l, particle size distribution <100 μm, max. 5%; >500 μm, max. 2%). The fluidizing gas used was nitrogen. The temperature in the fluidized bed was 300° C. and the residence time was about 2 seconds. The vapor mixture leaving the fluidized bed was condensed.

The condensate was found to contain 292 g of caprolactam and 4 g of oligomer/polymer. The yield of caprolactam was 97.3%, based on starting nylon-6.

EXAMPLE 2

100 g of oligomers of caprolactam (about 50% by weight of dimers and trimers, remainder: tetramers and higher oligomers) were suspended in 100 g of water and introduced into a 500 ml autoclave. The autoclave was purged with nitrogen and then heated to 200° C. After 30 minutes the contents of the autoclave were let down at 200° C. under a pressure of about 15 bar into the fluidized bed of a fluidized bed oven. The fluidized bed oven was packed with 600 g of $Al_2O_3$ (Puralox; see Example 1). The fluidizing gas used was nitrogen. The temperature in the fluidized bed was maintained at 300° C. The vapor mixture leaving the fluidized bed was condensed. 97 g of caprolactam were obtained after the water had been distilled off.

EXAMPLE 3

300 g of nylon-6 (relative viscosity 2.7; measured at a concentration of 1 g per 100 ml in 96% strength by weight sulfuric acid at 25° C.) were introduced into a 2 l autoclave together with 700 g of water and purged with nitrogen. Then the autoclave was heated to 280° C. After a residence time of 3 hours the contents of the autoclave were slowly let down without cooling directly into a fluidized bed oven packed with 1000 g of $Al_2O_3$ (Puralox; see Example 1). The $Al_2O_3$ was kept in a fluidized state with nitrogen. The temperature in the fluidized bed was 300° C. The vapor mixture leaving the fluidized bed was condensed. The condensate contained 280 g of caprolactam.

We claim:

1. A process for recovering caprolactam from oligomers and/or polymers of caprolactam, comprising the following steps:
   a) treating oligomers and/or polymers of caprolactam with from 1 to 20 parts by weight of water per part by weight of oligomer or polymer at from 200° to 350° C. under superatmospheric pressure with a residence time of from 0.5 to 10 hours in a liquid aqueous phase to form an aqueous reaction mixture comprising polycaprolactam, monomeric caprolactam and oligomers thereof, and
   b) passing the aqueous reaction mixture obtained in a) into a fluidized bed of alumina at from 250° to 400° C. to obtain a mixture of steam and caprolactam.

2. The process of claim 1, wherein the water is employed in an amount of from 2 to 10 parts by weight of water per part by weight of oligomer/polymer.

3. The process of claim 1, wherein stage a) is carried out at from 250° to 300° C.

4. The process of claim 1, wherein stage a) is carried out at a pressure of from 15 to 200 bar.

5. The process of claim 1, wherein stage a) is carried out with the additional presence of phosphoric acid or sodium hydroxide.

6. The process of claim 1, wherein stage b) is carried out at from 290° to 360° C.

7. The process of claim 1, wherein the alumina used is γ-alumina.

8. The process of claim 1, wherein the residence time in the fluidized bed is from 0.1 to 30 seconds.

9. The process of claim 1, wherein the aqueous reaction mixture of stage a) is passed into the fluidized bed of stage b) directly via a nozzle opening without prior depressurization.

* * * * *